US00PP25437P3

(12) United States Plant Patent
Vitten et al.

(10) Patent No.: US PP25,437 P3
(45) Date of Patent: Apr. 14, 2015

(54) STRAWBERRY PLANT NAMED 'DRISSTRAWTHIRTYEIGHT'

(50) Latin Name: *Fragaria×ananassa*
Varietal Denomination: DrisStrawThirtyEight

(71) Applicant: Driscoll Strawberry Associates, Inc., Watsonville, CA (US)

(72) Inventors: Matthias D. Vitten, Aptos, CA (US); Carlos D. Fear, West Malling (GB); Bruce D. Mowrey, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 166 days.

(21) Appl. No.: 13/815,230

(22) Filed: Feb. 12, 2013

(65) Prior Publication Data

US 2014/0230112 P1 Aug. 14, 2014

(51) Int. Cl.
*A01H 5/00* (2006.01)

(52) U.S. Cl.
USPC ..... Plt./209

(58) Field of Classification Search
USPC ..... Plt./209
See application file for complete search history.

*Primary Examiner* — Anne Grunberg
(74) *Attorney, Agent, or Firm* — Jondle & Associates, P.C.

(57) ABSTRACT

A new and distinct variety of strawberry plant named 'DrisStrawThirtyEight' particularly characterized by fully everbearing, vigorous, high yielding plants with firm, medium red fruit, is disclosed.

3 Drawing Sheets

Genus and species: *Fragaria×ananassa.*
Variety denomination: 'DrisStrawThirtyEight'.

BACKGROUND OF THE NEW PLANT

The present invention relates to a new and distinct strawberry variety designated 'DrisStrawThirtyEight' and botanically known as *Fragaria×ananassa*. This new strawberry variety was discovered in Kent, United Kingdom in August 2007 and originated from a cross between the proprietary female parent 'Driscoll Jubilee' (U.S. Plant Pat. No. 15,435) and the proprietary male parent 'Canterbury' (U.S. Plant Pat. No. 12,577). A single plant was selected and asexually propagated via tissue culture and vegetative cuttings in Kent, United Kingdom in 2007.

'DrisStrawThirtyEight' underwent further testing in Kent, United Kingdom for five years (2008-2012). The present invention has been found to retain its distinctive characteristics through successive asexual propagations via stolons and tissue culture.

Plant Breeder's Rights for this variety have not been applied for. 'DrisStrawThirtyEight' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Kent, United Kingdom.

1. Fully everbearing;
2. Vigorous, high yielding plants; and
3. Firm, medium red fruit.

DESCRIPTION OF THE PHOTOGRAPH

The accompanying color photographs show typical specimens of the new variety at various stages of development. The colors shown are as true as can be reasonably obtained by conventional photographic procedures. The photographs were taken from five to six month-old plants.

DESCRIPTION OF THE NEW VARIETY

Figure 1:
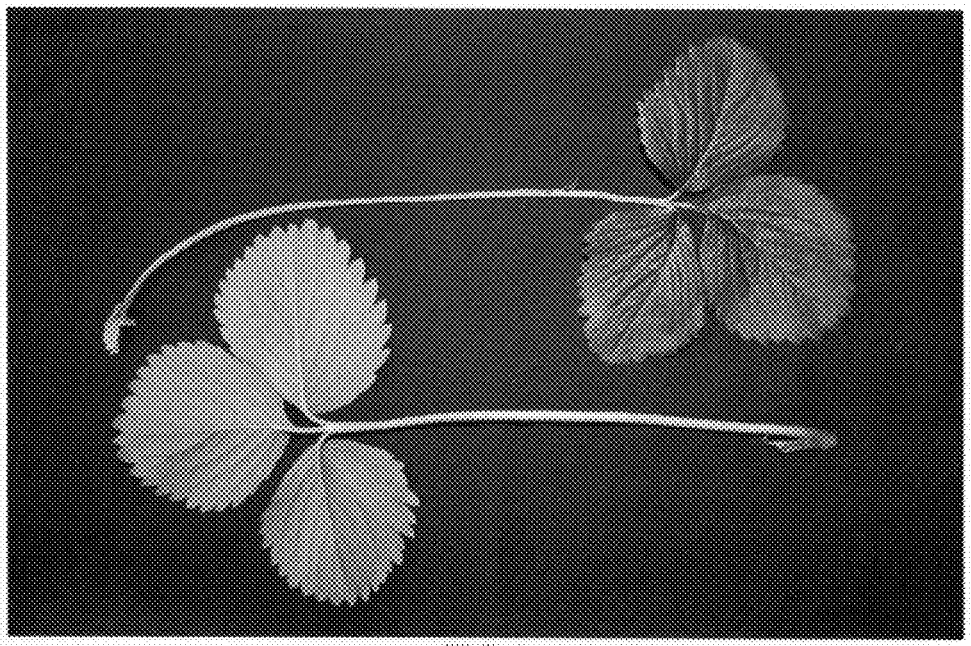
FIG. 1 shows upper and lower surfaces of the leaves of the plant with three leaflets.
Figure 2:
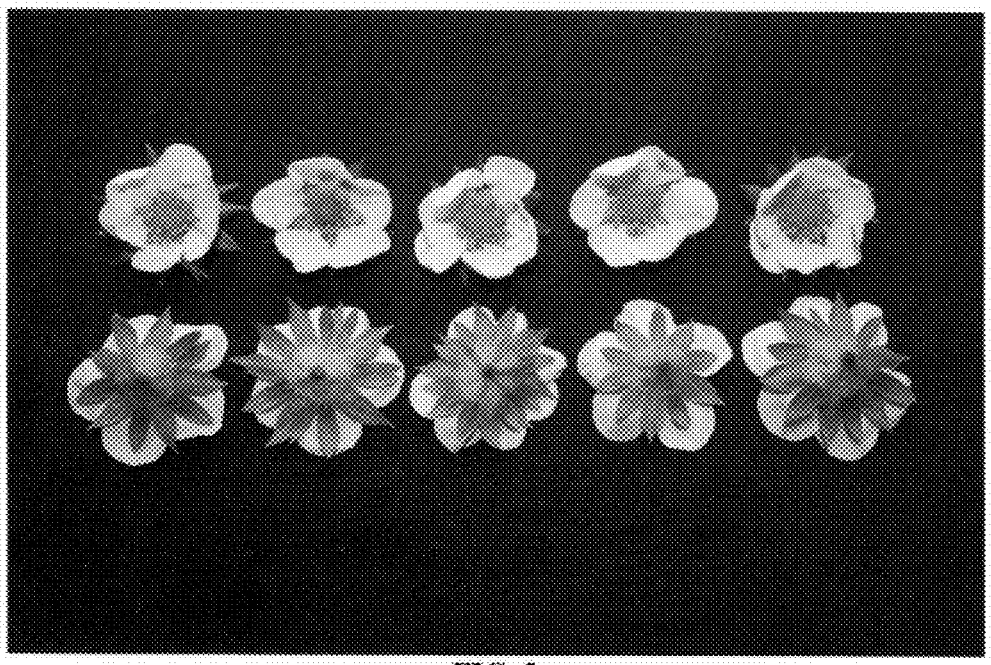
FIG. 2 shows the upper and lower surfaces of the flowers.
Figure 3:
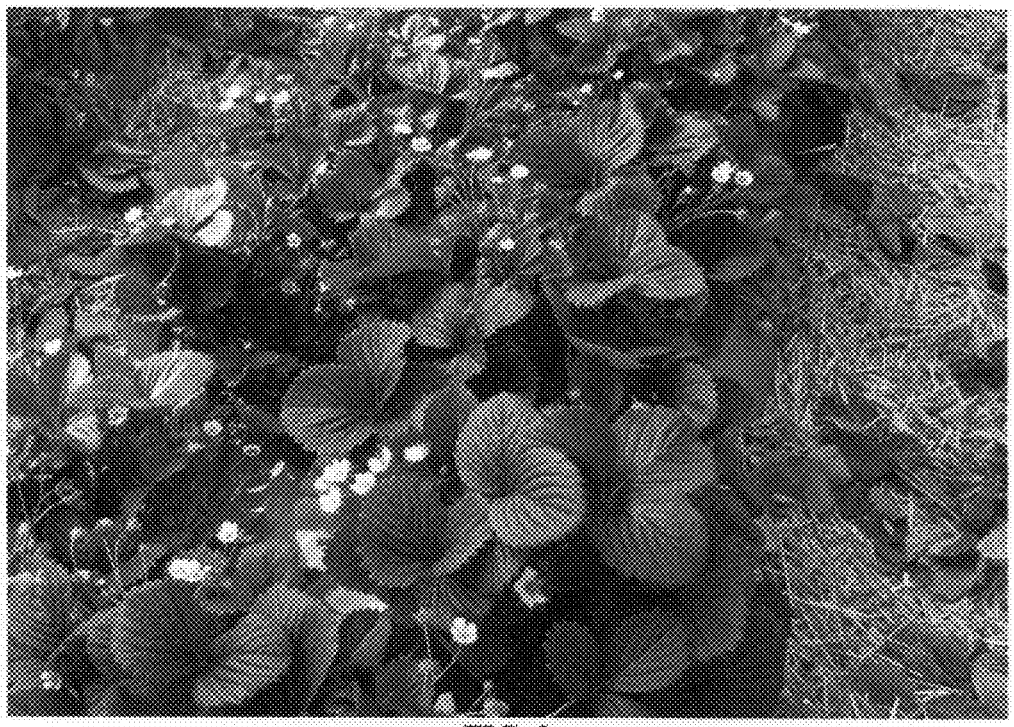
FIG. 3 shows whole plants with flowers and fruit.
Figure 4:
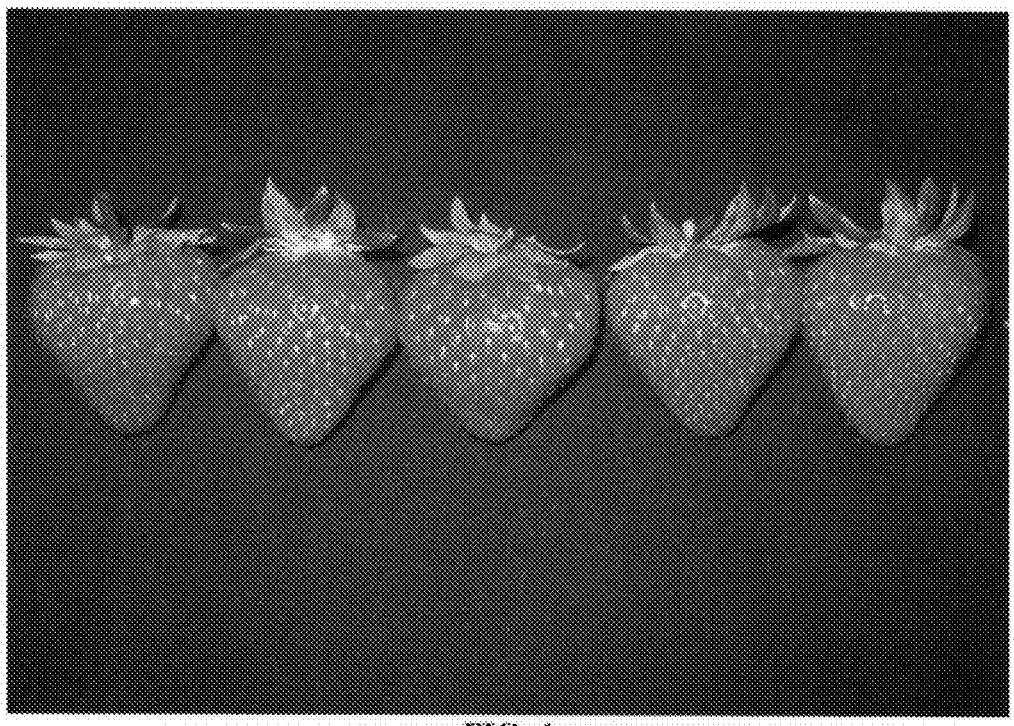
FIG. 4 shows the whole fruit.
Figure 5:
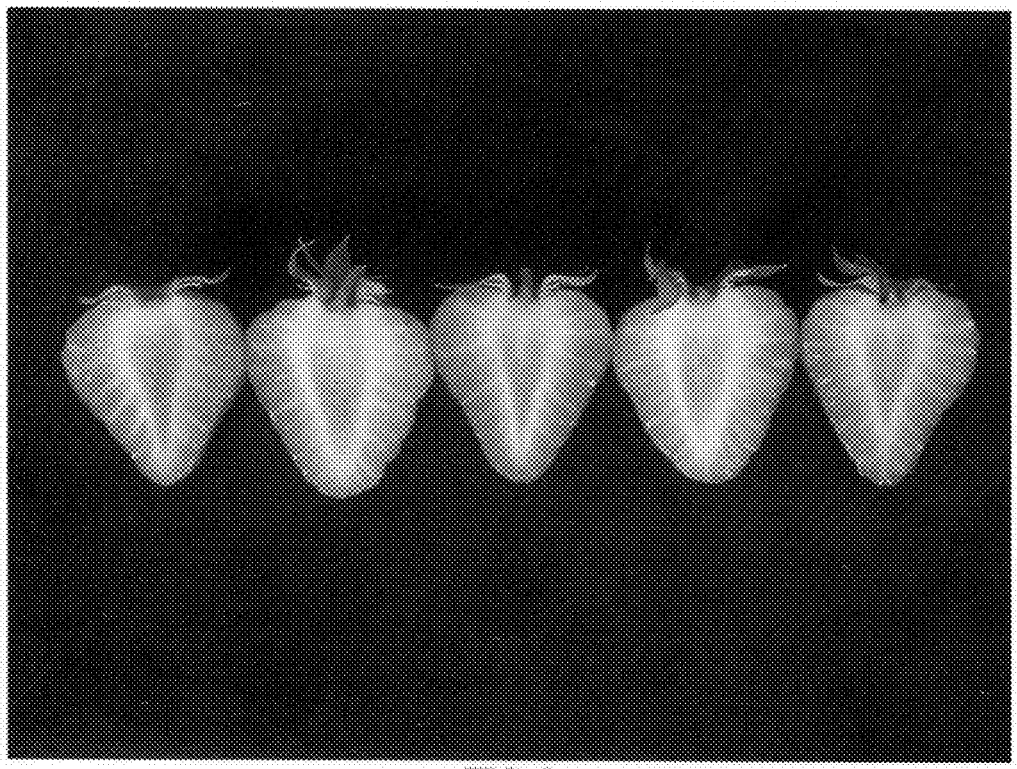
FIG. 5 shows the fruit in longitudinal cross-section.

The following detailed descriptions set forth the distinctive characteristics of 'DrisStrawThirtyEight'. The data which define these characteristics is based on observations taken in Kent, United Kingdom from 2008 to 2012. This description is in accordance with UPOV terminology. Color designations, color descriptions, and other phenotypical descriptions may deviate from the stated values and descriptions depending upon variation in environmental, seasonal, climatic, and cultural conditions. 'DrisStrawThirtyEight' has not been observed under all possible environmental conditions. The botanical description of 'DrisStrawThirtyEight' was taken from five to six month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION OF THE PLANT

Classification:

*Species.*—*Fragaria×ananassa.*
*Common name.*—Strawberry.
*Denomination.*—'DrisStrawThirtyEight'.

Parentage:
*Female parent*.—The proprietary variety 'Driscoll Jubilee' (U.S. Plant Pat. No. 15,435).
*Male parent*.—The proprietary variety 'Canterbury' (U.S. Plant Pat. No. 12,577).

Plant:
*Height*.—43.0 cm.
*Diameter*.—54.7 cm.
*Number of crowns/plant*.—3.
*Habit*.—Globose — semi-upright
*Density of individual plant*.—Medium.
*Vigor* (*health and hardiness of plant*).—Medium.

Terminal leaflets:
*Size*.—Medium. Length: 9.70 cm. Width: 8.55 cm. Length/width ratio: 1.1 (Longer than broad).
*Number of teeth/terminal leaflet*.—21.
*Shape of teeth*.—Obtuse — serrate to crenate.
*Color*.—Upper surface: RHS N137A (Medium green). Lower surface: RHS 137B (Medium green).
*Shape in cross section*.—Flat — straight.
*Blistering*.—Medium.
*Glossiness*.—Absent or weak.
*Number of leaflets*.—Three only.
*Shape*.—Oval.
*Base shape*.—Acute.
*Apex descriptor*.—Rounded.
*Variegation*.—Absent.
*Margin*.—Serrate.
*Margin profile*.—Revolute (margins rolled backwards).

Petiole:
*Length*.—Medium; 26.4 cm.
*Diameter*.—3.94 mm.
*Pubescence*.—Medium.
*Pose of hairs*.—Slightly upwards.
*Color*.—RHS 144B (Medium yellow-green).
*Bracts*.—Absent.

Petiolule:
*Length*.—10.83 mm.
*Diameter*.—2.73 mm.
*Color*.—RHS 144B (Medium yellow-green).

Stipule:
*Length*.—3.30 mm.
*Width*.—8.27 mm.
*Pubescence*.—Dense.
*Stipule anthocyanin coloration*.—Medium; RHS 47D (Medium red).

Stolon:
*Number*.—Medium.
*Average number of daughter plants per square foot*.—7.
*Anthocyanin coloration*.—Absent or very weak; RHS 145A (Light yellow-green).
*Diameter at bract*.—5.39 mm.
*Thickness*.—Medium.
*Pubescence*.—Medium.

Inflorescence:
*Position relative to foliage*.—Above.
*Number of flowers*.—Medium.
*Time of flowering* (*50% of plants at first flower*).—Medium; July 1$^{st}$-July 25$^{th}$.
*Flower size*.—Medium.
*Diameter*.—26.49 mm.
*Petals*.—Shape: Orbicular. Apex: Rounded. Base: Rounded. Margin: Entire. Spacing: Overlapping. Length: 11.24 mm. Width: 11.22 mm. Length/width ratio: 1.0 (As long as broad). Petal number per flower: 6. Color (upper surface): RHS NN155B (White).
*Calyx*.—Diameter: 25.82 mm. Diameter relative to corolla: Same size. Inner calyx diameter relative to outer: Same size. Insertion of calyx: Level. Pose of calyx segments: Spreading to outwards. Size of calyx in relation to fruit: Same size. Adherence of calyx: Medium.
*Sepal*.—Shape: Elliptical. Apex: Truncate. Margin: Entire. Length: 9.35 mm. Width: 4.45 mm. Sepal number per flower: 6.
*Receptacle color*.—RHS 151B (Medium yellow-green).
*Stamen*.—Present. Anther color: RHS 13A (Medium yellow).
*Pedicel*.—Attitude of hairs: Upwards.

Fruiting truss:
*Length*.—Medium; 37.7 cm.
*Diameter at base of truss*.—5.07 mm.
*Number of berries per fruiting truss*.—6.
*Attitude at first picking*.—Semi-erect.
*Color at base of truss*.—RHS 144C (Light yellow-green).

Fruit:
*Relative fruit size*.—Medium.
*Length*.—35.64 mm.
*Width*.—32.78 mm.
*Length/width ratio*.—1.1 (Longer than broad).
*Fruit hollow length*.—25.38 mm.
*Fruit hollow width*.—7.99 mm.
*Fruit hollow length/width ratio*.—3.2.
*Fruit hollow center* (*cavity*).—Small.
*Weight* (*per individual berry*).—18.76 g.
*Predominant fruit shape*.—Conical.
*Difference in shape between primary and secondary fruits*.—None or very slight.
*Evenness of fruit surface*.—Even or very slightly uneven.
*Fruit skin color*.—RHS 46B (Medium red).
*Evenness of fruit color*.—Even or very slightly uneven.
*Fruit glossiness*.—Weak.
*Achenes*.—Insertion of achenes: Level with surface. Coloration: Sunward side of berry: RHS 165B (Medium greyed-orange). Shaded side of berry: RHS 164A (Medium greyed-orange). Number per berry: 280.0. Weight (weight of achenes divided by total # seed): 0.6 mg. Width of band without achenes: Absent or very narrow.
*Firmness of flesh* (*when fully ripe*).—Firm.
*Color of flesh* (*excluding core*).—RHS 33A (Medium orange-red).
*Color of core*.—RHS 33A (Medium orange-red).
*Evenness of flesh color*.—Slightly uneven.
*Distribution of flesh color*.—Marginal and central.
*Sweetness*.—Medium; average 8.9 °Brix.
*Acidity*.—Medium.
*Texture when tasted*.—Fine.
*Type of bearing*.—Fully everbearing — fully remontant.
*Grams of fruit/plant*.—1100.0 g.
*Harvest interval*.—Late June to early October.
*Harvest maturity*.—Late.

Disease and pest resistance:
*Botrytis fruit rot*.—Moderately resistant.
*Powdery mildew*.—Moderately resistant.
*Verticillium wilt*.—Moderately resistant.

Reaction to stress: None observed.

COMPARISON WITH PARENTAL AND COMMERCIAL VARIETIES

When 'DrisStrawThirtyEight' is compared to the female parent plant 'Driscoll Jubilee' (U.S. Plant Pat. No. 15,435), 'DrisStrawThirtyEight' has much higher fruit yield, heavier stipule pubescence, and firmer fruit than 'Driscoll Jubilee'.

When 'DrisStrawThirtyEight' is compared to the male parent plant 'Canterbury' (U.S. Plant Pat. No. 12,577), 'DrisStrawThirtyEight' is more vigorous, and has smaller, less sweet, and more acidic fruit than 'Canterbury'.

When 'DrisStrawThirtyEight' is compared to the commercial variety 'DrisStrawTwo' (U.S. Plant Pat. No. 18,878), 'DrisStrawThirtyEight' has medium leaf blistering, absent or very weak stolon anthocyanin coloration, and an absent or very narrow width of band without achenes, whereas 'DrisStrawTwo' has strong leaf blistering, strong stolon anthocyanin coloration, and a medium width of band without achenes. Additionally, 'DrisStrawThirtyEight' has weak fruit glossiness, whereas 'DrisStrawTwo' has strong fruit glossiness.

When 'DrisStrawThirtyEight' is compared to the commercial variety 'Driscoll Camarillo' (U.S. Plant Pat. No. 14,771), 'DrisStrawThirtyEight' has an average of 3 crowns per plant, a medium plant density and conical shaped fruit with weak glossiness, whereas 'Driscoll Camarillo' has an average of 4.8 crowns per plant, an open plant density and cordate shaped fruit with strong glossiness.

We claim:

1. A new and distinct variety of strawberry plant named 'DrisStrawThirtyEight' as described and illustrated herein.

* * * * *